US006992775B2

(12) United States Patent
Soliz et al.

(10) Patent No.: US 6,992,775 B2
(45) Date of Patent: Jan. 31, 2006

(54) HYPERSPECTRAL RETINAL IMAGER

(75) Inventors: Peter Soliz, Albuquerque, NM (US); Leonard John Otten, III, Placitas, NM (US); Paul Wiley Truitt, Albuquerque, NM (US)

(73) Assignee: Kestrel Corporation, Albuquerque, NM (US)

( * ) Notice: Subject to any disclaimer, the term of this patent is extended or adjusted under 35 U.S.C. 154(b) by 0 days.

(21) Appl. No.: 10/651,491

(22) Filed: Aug. 29, 2003

(65) Prior Publication Data

US 2004/0085542 A1    May 6, 2004

Related U.S. Application Data

(60) Provisional application No. 60/407,330, filed on Aug. 29, 2002.

(51) Int. Cl.
  *G01B 9/02* (2006.01)
(52) U.S. Cl. ................................................. 356/456
(58) Field of Classification Search ................ 356/451, 356/456; 250/339.08, 339.09
  See application file for complete search history.

(56) References Cited

U.S. PATENT DOCUMENTS

| | | | |
|---|---|---|---|
| 5,539,517 A | | 7/1996 | Cabib |
| 5,784,162 A | | 7/1998 | Cabib |
| 6,051,835 A | * | 4/2000 | Pettipiece et al. .......... 356/456 |
| 6,128,532 A | | 10/2000 | Kato |
| 6,142,829 A | | 11/2000 | Adel |
| 6,198,532 B1 | * | 3/2001 | Cabib et al. ................ 356/456 |
| 6,276,798 B1 | | 8/2001 | Gil |
| 6,556,853 B1 | | 4/2003 | Cabib |

OTHER PUBLICATIONS

Hyperspectral Fundus Imager, Truitt et al, Poceedings of SPIE vol. 4132( 2000), pp. 356-364.*

Butler, E. & Otten, L. Low Cost Multi-Spectral Imager for Environmental Surveying From a Light Aircraft. First International Remote Sensing Conference and Exhibition. (1994). Strasbourg, France.

Geeraets, W.J., Williams, R.C., Chan, G., Ham Jr., W.T., Guerry III. D., & Schmidt, F.H. The Relative Absorption of Thermal Energy in Retina and Choroid. Investment Opthalmology. Jun., 1962; 1:340-7.

Hammer, M., Schweitzer, D.S., Leistritz, L., Scibor, M., Donnerhacke, K., & Strobel, J. Imaging Spectroscopy of the Human Ocular Fundus in Vivo. Journal of Biomed Optics. (1997). 2, 418-425.

Meigs, A.D., Otten, L.J., Butler, E., Jones, B., Portigal, F. Seller, R., & O'Hair, J. Kestrel's New FTVHSI Instrument for Hyperspectral Remote Sensing. SPIE (1996). vol. 2960.

(Continued)

*Primary Examiner*—Samuel A. Turner
(74) *Attorney, Agent, or Firm*—Janeen Vilven; Peacock Myers, P.C.

(57) ABSTRACT

An ophthalmic instrument (for obtaining high resolution, wide field of area hyperspectral retinal images for various sized eyes) includes a fundus retinal imager, (which includes optics for illuminating and imaging the retina of the eye); apparatus for generating a real time image of the area being imaged and the location of the hyperspectral region of interest; a high efficiency spatially modulated common path Fourier transform hyperspectral imager, a high resolution detector optically coupled to the hyperspectral and fundus imager optics; and a computer (which is connected to the real time scene imager, the illumination source, and the high resolution camera) including an algorithm for recovery and calibration of the hyperspectral images.

10 Claims, 11 Drawing Sheets

OTHER PUBLICATIONS

Otten, L.J., Meigs, A.D., Sellar, R.G., & Rafert, J.B. Measured Performance of an Airborne Fourier Transform Hyperspectral Imager. Imaging Spectrometry II. SPIE Proceedings. 2819. (1996) Denver, CO.

Kafert, J., Sellar, R., & Blatt, J. Monolithic Fourier-Transform Imaging Spectrometer Applied Optics 34, (1995). 7228-7230.

Sweedler, J. & Denton, M. Spatially Encoded Fourier Transform Spectroscopy in the Ultraviolet to Near- Infrared. Applied Spectroscopy 34, (1989). 1378-1384.

Truitt, P.W., Soliz, P., Farnath, D. & Nemeth, S. Utility of Color Information for Segmentation of Digital Retinal Images: Neural Network-Based Approach. SPIE Medical Imaging Symposium. (1998) San Diego, CA.

Truitt, P.W., Ogawa, G.S.H., Soliz, P. & Nemeth, S.C. Multi-Spectral Imaging of the Fundus: An Alternative to Standard Color Photography for Improved Feature Detection and Diagnosis. Association for Research in Vision and Opthalmology (ARVO). (1998). Ft. Lauderdale FL.

* cited by examiner

HYPERSPECTRAL RETINAL IMAGER

CROSS REFERENCE TO RELATED APPLICATIONS

This application claims benefit under 35 U.S.C. § 119(e) of provisional application No. 60/407,330, filed Aug. 29, 2002, which is incorporated by reference herein, in its entirety, for all purposes.

STATEMENT OF GOVERNMENT INTEREST

This invention was made with government support under Contract No. 2000-153-KESTREL-SOLIZ awarded by the National Medical Technology Testbed, Inc. The government has certain rights in the invention.

FIELD OF THE INVENTION

The present invention relates to obtaining hyperspectral images of a field of view provided by an optical system. More particularly, the present invention relates to a fundus retinal imaging system that provides early diagnosis of various pathologies of the eye.

BACKGROUND OF THE INVENTION

The ability to resolve the fine spectral and spatial details on the retina can play a key role in the early diagnosis of vision loss. There is strong evidence linking certain retinal biochemical and physical changes to increased risk of developing vision losses. These preclinical features cannot be observed directly with today's imaging systems.

One proposed solution to the foregoing problems is to use a hyperspectral optical imaging system to measure the fine spectral and spatial features, and then processing and analyzing hyperspectral images of the retina obtained from the hyperspectral optical imaging system. Through hyperspectral imaging, these features would be preclinically detected and spectrally/spatially characterized. This type of phenotyping of lesions would help researchers and clinicians better classify biochemical profile of the disease and/or to detect abnormal cellular structures.

Various proposed approaches to this solution have been demonstrated. Collectively, a fundus imager (which is used to make an image of the retina) combined with spectral encoding optics (which is used to create the spectral signature from the image of the retina) is commonly referred to in this art as a hyperspectral imager system. A flash source is used with such an instrument to collect an image of the retina. This image is then relayed to a Fourier transform hyperspectral imager where the interferometer is set such that there is a separation between the two beams containing the image by rotating an optical element. The two beams are then interfered and the resulting image recorded, encoding one modulation of the full spectrum of the image. The optical element is then rotated a small amount and a second imager is collected using a second flash and this image is recorded, collecting a second modulation. This process is continued until a full set of separations that allow recovery of the desired optical spectrum.

The entire process can take up to several minutes. After collection, the images must be registered to assemble a spatially aligned data set that can then be Fourier transformed to produce a hyperspectral image. For example, U.S. Pat. Nos. 5,539,517, 5,784,162, 6,142,629, 6,129,532, 6,276,798, and 6,556,853 may be referred to for details of optical systems for obtaining Fourier transform spectral images based on a rotationally modulated common path interferometry (also known as a "Barns interferometry"). A major problem for the imagers disclosed is the inability to simultaneously record the entire spectral signature for an imaged area before the eye has moved. Registration is necessary with these imagers because the eye shifts slightly between successive images due to saccades, an involuntary motion of the eye.

The above described instrumentation has a number of significant limitations. Numerous exposures are required and it takes a long time to record a complete spectra. Both spatial and spectral registration are required. It is also necessary to use movable optical elements within the hyperspectral element. The apparatus is rotationally modulated, and provides no control of the spectra or duration of the illumination sources.

BRIEF SUMMARY OF THE INVENTION

One aspect of the present invention is that it provides an optics system with both high spectral resolution and high spatial resolution.

Another aspect of the present invention provides a hyperspectral retinal image having improved quality from a clinical device, to thereby enable an improved level of opthalmic healthcare.

Yet another aspect of the present invention is embedded data processing techniques that retrieve the hyperspectral image from the raw interference data collected by a hyperspectral imager.

Still another aspect of the present invention provides a fundus based ophthalmic hyperspectral imager instrument that records spectral signature simultaneously across a region on the retina.

Another aspect of the present invention provides a controllable fundus illumination light source that allows selection of both the duration of the light and the spectral bandwidth of the light.

Another aspect of the present invention is registration of the location of the hyperspectral image on the retina through the use of an auxiliary camera.

Another aspect of the present invention is embedded calibration sources that monitor the spectral radiance of the illumination light source and encode a spectral calibration reference on every image.

Yet another aspect of the present invention is the recovery of spectra of a region of the retina with a single exposure of the subject's eye to the light source.

Yet another aspect of the present invention is collection of a hyperspectral image of the retina with a hyperspectral imager whose optical components are fixed with respect to one another.

Yet another aspect of the present invention is the use of variable sized optics, to accommodate different sizes of eyes, for collecting hyperspectral retinal images on both human and non-human subjects.

Another aspect of the present invention is the provision of an affordable attachment to existing fundus retinal imagers.

Another aspect of the present invention provides for the identification of biomarkers to predict eye injury, cancer, eye disease, or drug efficacy or for toxicity testing.

Another aspect of the present invention is the generalized usefulness of the disclosed imager to be coupled to many different kinds of viewing instruments, such as microscopes, endoscopes, dermascopes, and broncoscopes.

Yet another aspect of the present invention is that it is useful to assess functional information about the retina by use of advanced statistical analysis techniques on hyperspectral images obtained using an apparatus according to the present invention.

It is yet another aspect of the present invention to increase the sensitivity of retinal diagnosis.

It is yet another aspect of the present invention to improve diagnosis of eye disease with improved retinal imaging techniques.

It is a further aspect of the present invention to isolate the signals representing the various retinal conditions using principal component analysis (PCA).

It is yet another aspect of the present invention to use Blind Source Separation (BSS) and Independent Component Analysis (ICA) to find the underlying factors associated with the recorded retinal image data.

It is yet another aspect of the present invention to apply non-linear independent component analysis to the separation of the sources present during the imaging of a retina the retina.

These and aspects of the present invention will become apparent from a review of the general and detailed description to follow.

According to one embodiment of the present invention, the apparatus is an ophthalmic instrument having a wide field of view and including a fundus imager, a scene camera, a spatially modulated common path Fourier transform hyperspectral imager optical system coupled to the fundus imager optics, a high resolution detector optically coupled to the hyperspectral imager optics and the fundus imager; a pair of calibration sources, and a computer. The field of view of the ophthalmic instrument apparatus is as wide as up to 30 degrees. The fundus imager includes optics for illuminating and imaging the retina and related structures of the eye. The scene camera may be considered to be a "registration camera." The scene (or "registration") camera is optically coupled to the imager optics for aligning the fundus imager to the eye and for locating the region of the hyperspectral image on the retina. The common path spatially modulated Fourier transform hyperspectral imager optical system is coupled to the fundus imager optics to simultaneously encode the entire spectral signature of the region being examined. The pair of calibration sources insert optical signals onto the hyperspectral image to provide spectral and radiometric calibration. The computer is connected to the illuminating optics, the scene camera, and the high resolution detector, and implements an algorithm for controlling the duration and spectral bandwidth of the illumination light provided by the illuminating optics. The computer also provides a graphical user interface whereby a user may control the apparatus. Optionally, a set of optics is provided with the ophthalmic instrument that can be used to adapt the instrument for observing various sized eyes.

In another embodiment of the present invention, the Fourier transform hyperspectral imager optical system includes imaging optics, one or more adjustable apertures to vary the amount of light entering the hyperspectral imager, a fixed configuration three element common path interferometer, a Fourier lens set, and a cylindrical imaging lens set to image the hyperspectral image onto the high resolution detector. The fixed configuration three element common path interferometer may be embodied as including a beam splitter and two folding mirrors. The beam splitter may be of either a conventional design or a compound design.

In one embodiment of the present invention, the scene camera includes a movable mirror that diverts the image from the fundus imager away from the hyperspectral imager to a high resolution imager whose output is used by the operator to align the imager to the eye. The light source includes two illumination sources that are optically coupled to the fundus imager. The first light source is a low power continuously-controlled intensity source filtered to prevent any harmful infrared and ultraviolet light from being directed to the eye by the fundus imager. The light directed into the eye from this first light source is reflected by the retina and this reflected light is imaged by the scene camera for alignment purposes. The second light source is a high brightness continuous source optically filtered to remove harmful infrared and ultraviolet light and then optically filtered to provide selectable optical bandwidth light that is directed to the eye by the fundus imager. The light directed into the eye from this second light source is reflected by the retina and this reflected light is used by the hyperspectral imager optics to collect a hyperspectral image of the selected region of the retina.

The light sources contains appropriate shutters to control the duration of the illumination, prevent simultaneous illumination by both sources, and provide fail safe control of the light to prevent accidental hazardous illumination of the subject. A first optically coupled reference for monitoring the spectral radiance of the bright light source is used to access a sample of the bright light prior to its being directed to the eye by the fundus imager. This sample is inserted into the Fourier transform hyperspectral image at the aperture. A second optically coupled reference for calibrating the spectral performance of the hyperspectral imager connects a calibration light source, such as a gas discharge lamp or laser, to the aperture of the hyperspectral imager. The optical set used to adapt the instrument to various sized eyes includes replaceable field and aperture stops, field lens, hole coupling optics, and illumination source geometry modifying optics.

A computer (general purpose or special purpose) controls and times the shutters in the light source, controls and times the transfer of the fundus image to the scene camera and hyperspectral optical system, controls, times, displays, and records the images of the scene and hyperspectral imager cameras, calculates and displays the data being collected and provides controls used to operate the system.

The instrument also includes a plurality of filters and algorithms to account for the reflectance of various wavelengths of light from different depths within the retina. The filters implement a means for optimizing the spectral band where specific wavelengths will be detected. The algorithms enable the calibration of measured light in terms of its spectra and its reflectance. Flash to flash variations, vignetting, and artifacts from conversion of the interferogram are removed by the algorithms.

According to one embodiment of the present invention, a large format, high resolution detector is used in order to enable the instrument to have a wide field of view.

Although the present invention is described in the illustrative embodiments as being used for imaging the fundus of the eye, an instrument according to the present invention may be embodied without retinal imager optics and is then referred to as being a hyperspectral imager optics system. The hyperspectral imager optics system is useful in association with a number of commercial imagers, for example, fundus scopes, endoscopes such as broncoscopes, and cystoscopes, dermascopes and microscopes.

The foregoing and other objects will be apparent from the following disclosure read in conjunction with the accompanying drawing figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

As noted above, the present invention is a system and method for obtaining hyperspectral images of a field of view provided by an optical system such as a fundus retinal imaging system. The present invention provides hyperspectral images of the retina to permit early diagnosis of various pathologies of the eye.

Figure 1:
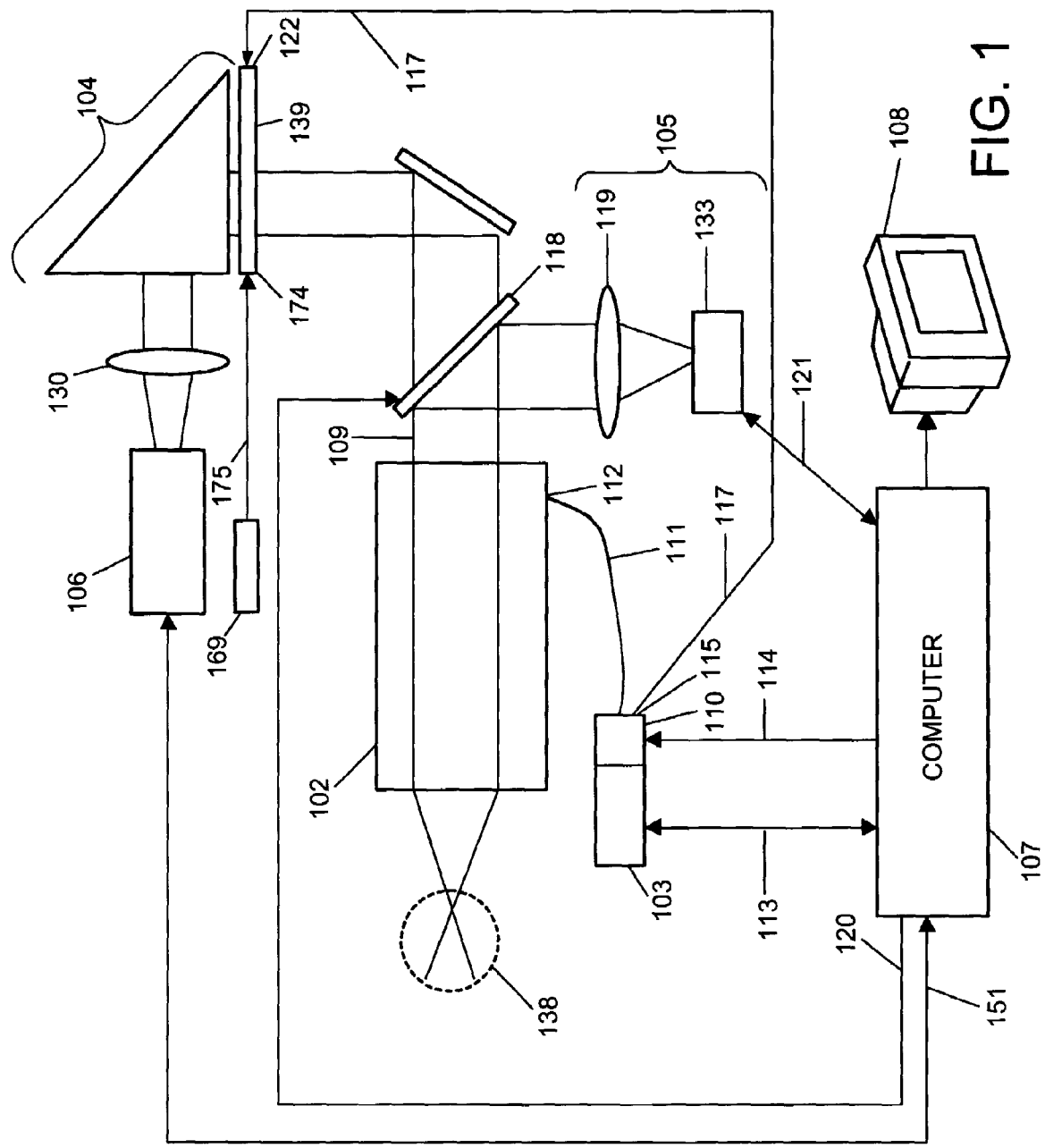
FIG. 1 illustrates a hybrid block diagram and optical schematic according to one embodiment of the present invention, including a fundus imager.

Referring to FIG. 1, a hybrid block diagram and optical schematic of one embodiment of the present invention is illustrated. A fundus retinal imager 102 observes an eye 138 and provides a collimated output 109. The fundus retinal imager 102 may be a JST ZOMZ, Model KFG 2, Zeiss FF4, FF5, FF450, the Topcon TRC-50 series, the Canon CF-60 series or CR5-45 and others can also be used, as one skilled in the art will appreciate. A light source 103 and an optical filter assembly 110 are connected to the fundus retinal imager 102 via a fiber optic cable 111 and a fiber optic port 112 provided on fundus retinal imager 102. The light source 103 includes two continuously lit illumination lamps (not shown), such as a tungsten, xenon, or metal halide, which are controlled by a computer 107 via a control connection 113. One lamp (not shown) is a low brightness lamp used to align the instrument to the eye 138, and the other lamp (not shown) is a high brightness lamp used to illuminate the eye for the gathering of the hyperspectral data. The light source 103 includes UV and IR filters (not shown) to block harmful radiation.

The filter assembly 110, which is controlled by the computer 107 via a control line 114, includes plural filters for use in creating custom spectral observation bands. The fundus retinal imager 102 includes UV and IR blocking filters (not shown) to avoid damaging the eye through illumination in these bands. The filter assembly 110 also includes a mechanism (not shown) for selectively positioning a particular one of the plural filters in the optical path between the source 103 and the fiber optic cable 111. Use of a filtered light source reduces the intensity of the illumination on the subject by applying only the light band of interest making the examination less invasive.

The light source 103 has shutters (not shown) controlled by the computer 107 through the control connection 113 that are used to select the light source and control its duration. The shutters are used as a safety feature to prevent light from entering the eye except as commanded by the operator. The light source 103, has an optical fiber 117 placed so as to receive the light from beam coupler 115 and connected to port 139 on the input aperture 122 of the Fourier transform spectral interferometer to insert an illumination reference 560 (refer to FIG. 5A) on the edge of the interference pattern 556 (refer to FIG. 5A). In addition, a spectral calibration source (for example, a mercury gas discharge lamp) 169 is connected by fiber optics 175 to a port 174 on the other side of the input aperture 122 to insert a spectral calibration signal 565 (refer to FIG. 5A) onto the other edge of interferometric image 556 (refer to FIG. 5A). The input aperture 122 is replaceable, thereby allowing apertures of different widths to be installed to increase the signal admitted to the hyperspectral imager 104 for low light observations. As those familiar with Fourier transform spectrometry will appreciate, such changes do not affect the spectral resolution of the instrument.

The scene camera 105 includes a movable mirror 118 (see also the movable mirror 418 of FIG. 4), an imaging lens 119 (see also the imaging lens 419 of FIG. 4), and a CCD detector 133, the image plane of which is positioned in the focal plane of the imaging lens 119. The movable mirror 118 is connected to the computer 107 via a control cable 120. The detector 133 is connected to the computer 107 via a control and data cable 121. The detector 133 may be satisfactorily embodied as a commercially available large format sensor. The output from the fundus imager 102 passes through the movable mirror 118 location, when the mirror is commanded by the computer 107 not to be in a position that reflects the image to the scene camera 105, to the input to the Fourier transform common path interferometer. Output from the Fourier transform common path interferometer 104 is imaged through a lens set 130 onto a data detector 106.

Control of the detector 106 and the image signal from the detector 106 is sent to the computer 107 via a signal and control coupling 151.

Figure 4:
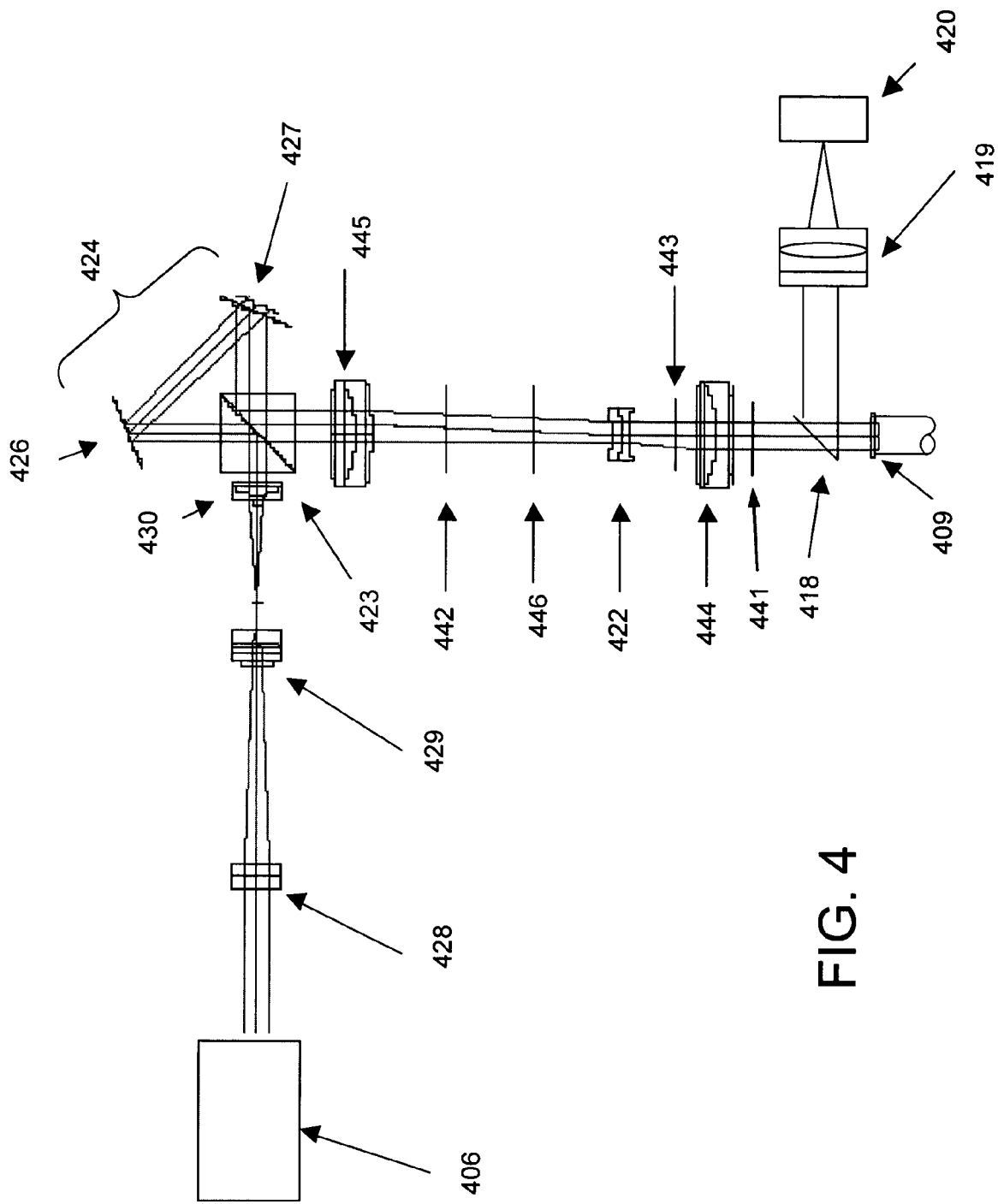
FIG. 4 illustrates an optical layout according to one embodiment of the present invention.

Referring to FIG. 4, the optical layout according to one embodiment of the present invention is illustrated. Light from the fundus imager 409 can be diverted by the flip mirror 418 via the scene camera object lens 419 to the scene camera 420 or to the hyperspectral imager. A common path spatially modulated Fourier transform interferometer is where the two dimension image from the fundus imager 409 is converted into a one dimensional image by an aperture 442 and lenses 444, 422, 445. This one dimensional image is then relayed through a beam splitter 423 that can be either a conventional type 423, or a high efficiency type 625 (refer to FIG. 6). In the conventional configuration 424, one dimensional images are split into two equal components by a beamsplitter 423, which are then folded by two mirrors 426, 427 before being recombined in the beam splitter 423 and projected toward a set of imaging lenses 428, 429, 430. In conjunction with the beam splitter 423, the two mirrors 426, 427 are positioned such that they introduce separation in the two optical beams such that the two beams will interfere on the detector 406 when recombined in the beam splitter 423 and projected by the lens set 428, 429, 430 onto the high-resolution detector 406 placed in the image plane of the lens set 428, 429, 430, which image only the long spatial dimension of the aperture 442.

Figure 6:
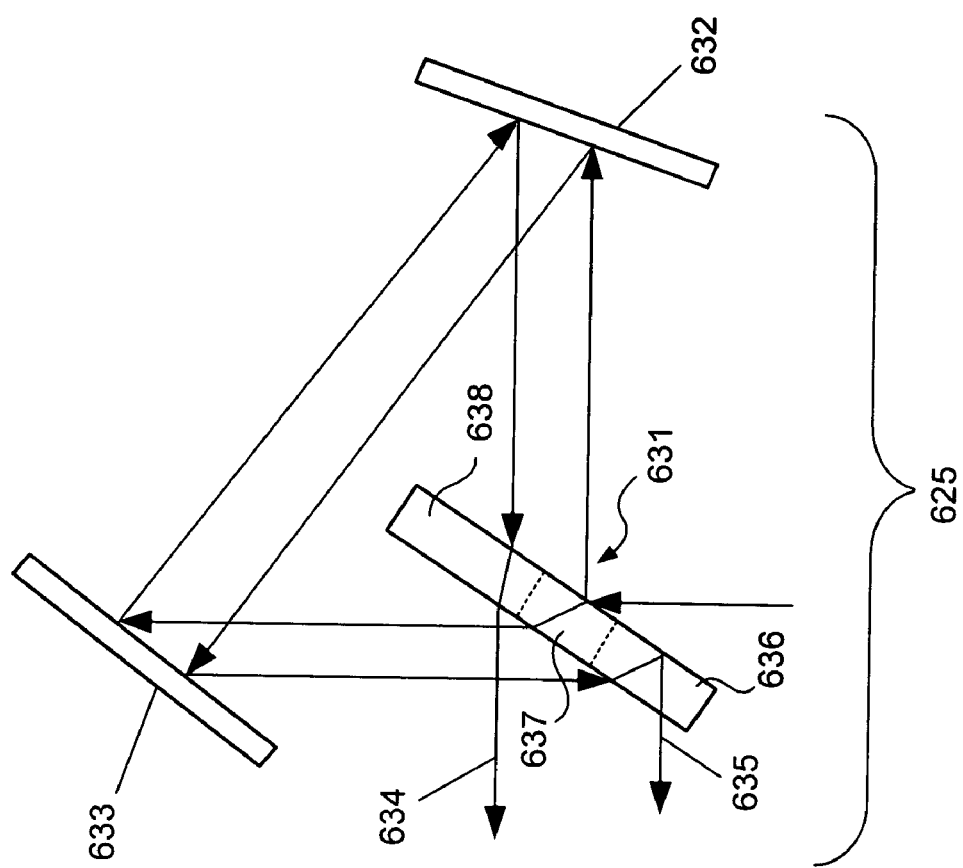
FIG. 6 illustrates a high efficiency optical layout according to another embodiment of the present invention.

Referring to FIG. 6, a high efficiency optical layout according to another embodiment of the present invention is illustrated. With the high efficiency configuration 625, the beam splitter 631 is divided into three regions, fully reflective 636, half transmissive and half reflective 637, and fully transmissive 638, such that there is no loss of optical energy out the input. The two mirrors 632, 633 are positioned such that they introduce separation in the split optical beams 634, 635 such that the two beams will interfere when recombined through beam splitter 631 and a set of imaging lenses onto a high-resolution detector 406 (refer again to FIG. 4) placed in the image plane of imaging lens set. It is noted that with the high efficiency beam splitter 631 none of the light entering the common path interferometer is lost as happens with the conventional beam splitter 423.

Referring to FIG. 6, a high efficiency optical layout according to another embodiment of the present invention is illustrated. With the high efficiency configuration 625, the beam splitter 631 is divided into three regions, fully reflective 636, half transmissive and half reflective 637, and fully transmissive 638, such that all of the optical energy is directed to the detector. The two mirrors 632, 633 are positioned such that they introduce separation in the split optical beams 634, 635 such that the two beams will interfere when recombined through beam splitter 631 and a set of imaging lenses onto a high-resolution detector 406 (refer again to FIG. 4) placed in the image plane of imaging lens set. It is noted that with the high efficiency beam splitter 631 none of the light entering the common path interferometer is lost as happens with the conventional beam splitter 423 when used in a common path interferometer.

Figure 2:
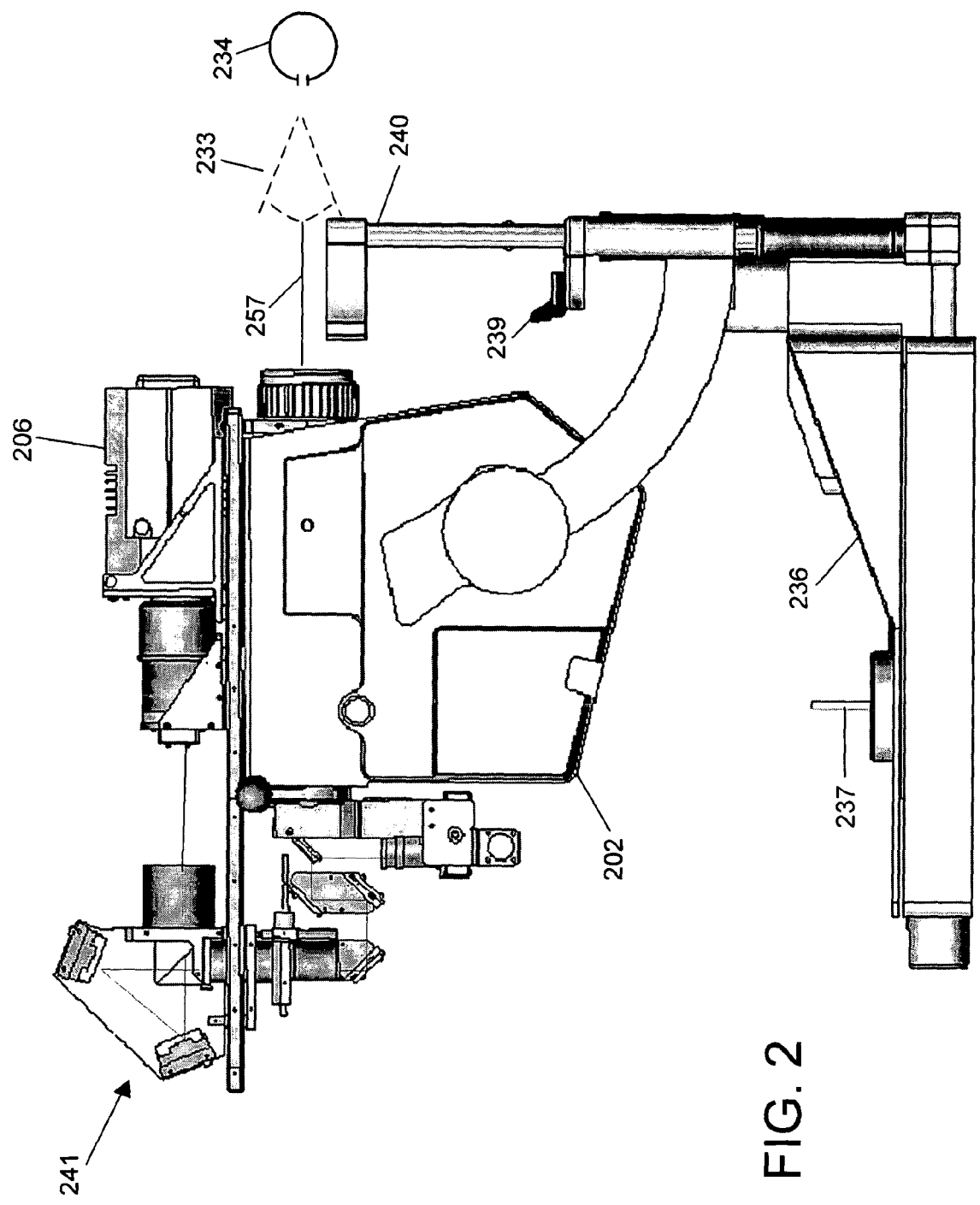
FIG. 2 illustrates a side elevation view of a fundus retinal imager in association with the housings for the improved hyperspectral imager optics and high resolution camera according to one embodiment of the present invention.

Referring to FIG. 2, a side elevation view of a fundus retinal imager in association with the housings for the improved hyperspectral imager optics and high resolution camera according to one embodiment of the present invention is illustrated. The fundus retinal imager 202 includes a base 236, a joystick control 237 for aligning the field of view of the system with the eye 233 of a patient. The fundus retinal imager 202 also includes a chin rest 239 and a forehead rest 240. The hyperspectral imager optics 241, and high resolution detector, 206, are supported by the fundus imager 202.

In operation, after the patient's eye has been dilated, the patient's head is properly positioned by the chin rest 239 and the forehead rest 240 so that the patient's eye is properly aligned with the optical axis 257 of the fundus retinal imager 202. Once in position, the low power lamp of the illumination source 103 (refer to FIG. 1) is directed to the eye by the fundus imager 202 upon opening the safety shutters. Proper alignment is then determined by viewing the live scene from the scene camera detector 133 (refer to FIG. 1) on a monitor 108 (refer to FIG. 1). Using real time images of the live scene the operator locates the region on the retina where the hyperspectral data is desired and adjusts the alignment accordingly.

Figure 3:
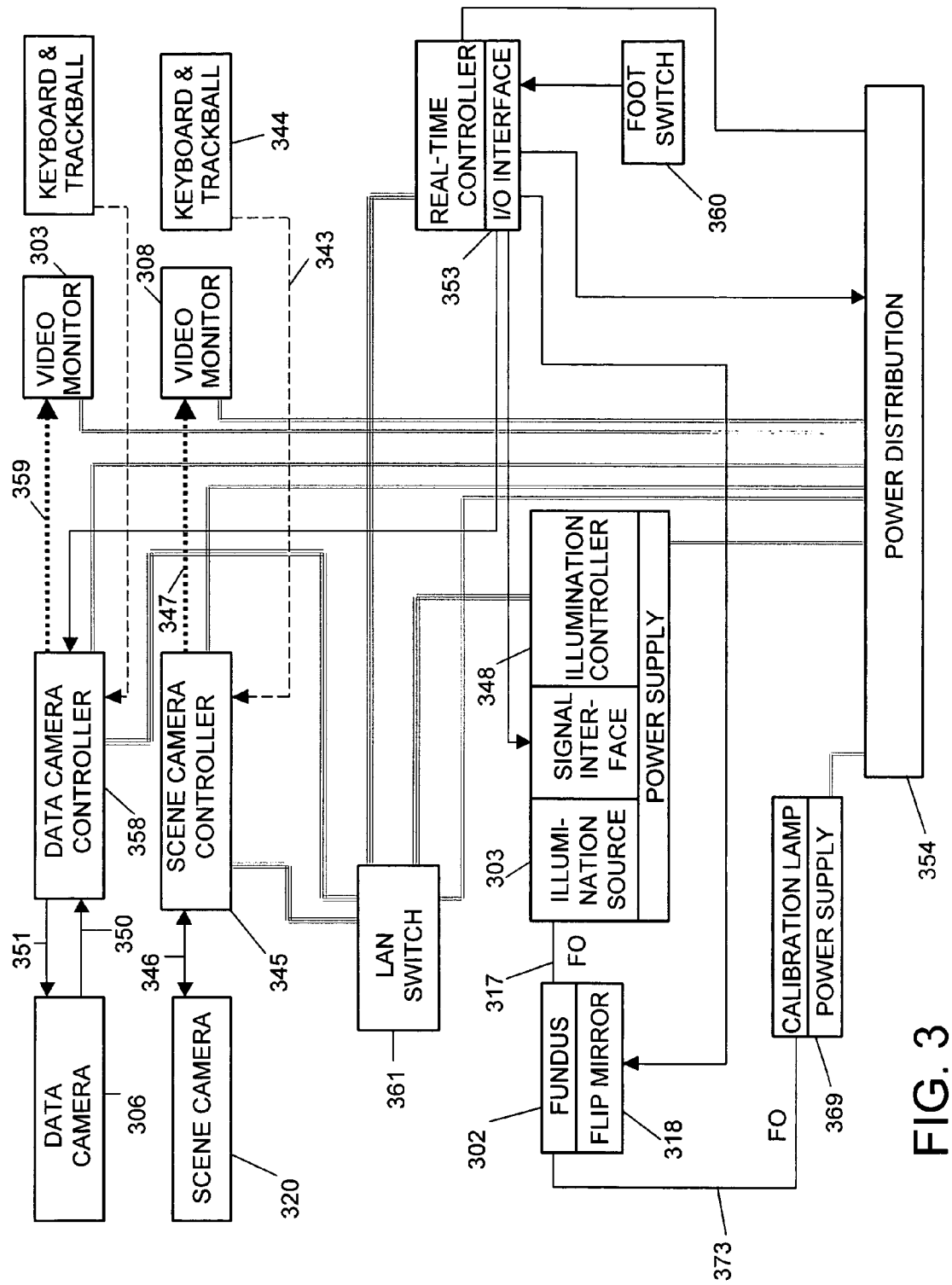
FIG. 3 illustrates a schematic diagram of the principal software controls and data flow according to one embodiment of the present invention.

Referring to FIG. 3, a schematic diagram illustrating the principal software controls and data flow of one embodiment of the present invention is illustrated. The main program 1142 (refer to FIG. 11) operates a number of subroutines and hardware to control the various functions of the system including frame grabbing, the storage (both temporarily and permanently) of data, the processing of imagery, and the operation of the light source. The main program 1142 (refer to FIG. 11), implemented via the controller, initializes the system, and provides means for setting the system up, inserting the various operating parameters, and recording patient data through the I/O interface 353. A data interface 343, which is turned on and run by the main program 1142 (refer to FIG. 11) through keyboard and trackball 344, is used to supply live images of the retina to a monitor 308 from the scene camera 320 that runs continuously.

The scene camera detector 320 is connected to a corresponding controller 345 (implemented on a general purpose or special purpose computer) by data and control cable 346. The scene camera controller 345 is connected to the monitor 308 via a data cable 347. The lightbox subroutine 1148 (refer to FIG. 11), which is controlled by the main program 1142 (refer to FIG. 11), runs the fundus imager's electronics (e.g. illumination sources controls, shutters) via the illumination controller 348. The main program 1142 (refer to FIG. 11) is initialized with system startup 1140 (refer to FIG. 11) and includes an algorithm for operating, controlling, recording, and displaying the output from the scene camera 320. The main program 1142 (refer to FIG. 11) also controls the position of the flip mirror 318 and the timing of when this mirror is positioned such as to relay the fundus image to the scene camera 320 or to the hyperspectral imager 104 (refer to FIG. 1). Finally, the main program 1142 (refer to FIG. 11) also controls the data camera subroutine 1149 (refer to FIG. 11) which, in turn, controls the data interface 350, which grabs interferometric images off the data camera 306 via a control and data cable 351. Image data is transferred from the data camera 306 to a processing subroutine, which, is transferred to memory.

While the foregoing has described certain data interfaces 343, 346, 347, 350, 351, those skilled in the art will appreciate that alternate hardware/software combinations, such as a frame grabber, or FIREWIRE® can be used to capture the respective images from the detectors 320, 306. Power for all the operating systems is provided by a common distribution structure 354, and the interaction of the various components is handled by an internal LAN switch 361.

The hyperspectral imaging system encodes all the spectral information in a single exposure including data to spectrally calibrate the image from a calibration lamp 369, connected through fiber optic cable 373 and to compensate for the variation in illumination by the illumination source 303, which is coupled to the fundus imager via another fiber optic cable 317.

Figure 5B:
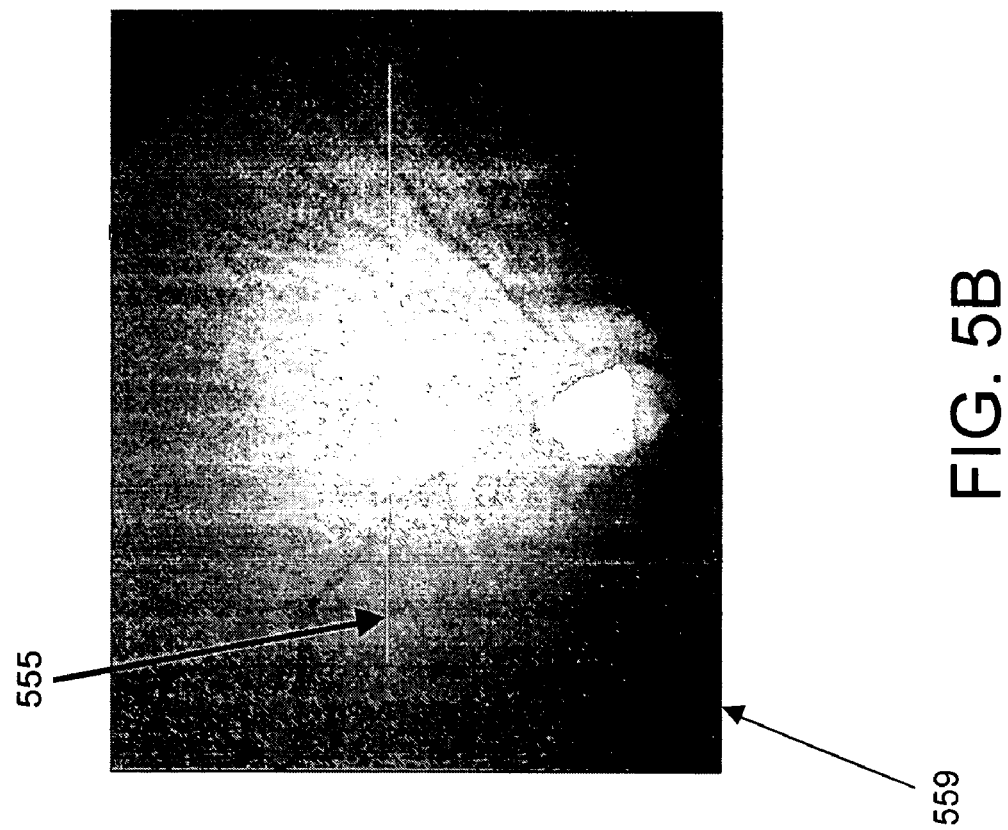
FIG. 5B illustrates an example of an image recorded by the scene camera with the corresponding location of the hyperspectral image annotated according to one embodiment of the present invention.

Referring to FIG. 5B, an example of an image recorded by the scene camera with the corresponding location of the hyperspectral image annotated according to one embodiment of the present invention is illustrated. Recording spatial and spectral data signatures for an imaged area of the eye before the eye has moved improves the image quality as is illustrated in FIG. 5B. An image of the complete hyperspectral image 556 (refer to FIG. 5A) of the region 555 illustrated in FIG. 5B is collected with one exposure. During the integration time for the data detector 406 (refer to FIG. 4), typically on the order of 50 msec, the eye remains motionless therefore avoiding any smearing of the region 555 being imaged.

In yet another embodiment of the present invention, the complete spectral signature is encoded during the integration time of the data detector 406 (refer to FIG. 4). This results in a further increase in the spectral and spatial accuracy of the hyperspectral image. Additionally, the number of exposures of the eye necessary to collect the desired data is reduced, thereby greatly reducing the discomfort of the examination for the subject. Because only one image is necessary to create the spectral signature, as opposed to the multiple images required by the prior art, the necessity of registering a series of successive images (which requires a considerable amount of processing time) and the inaccuracies inherent in such registering is avoided.

Figure 11:
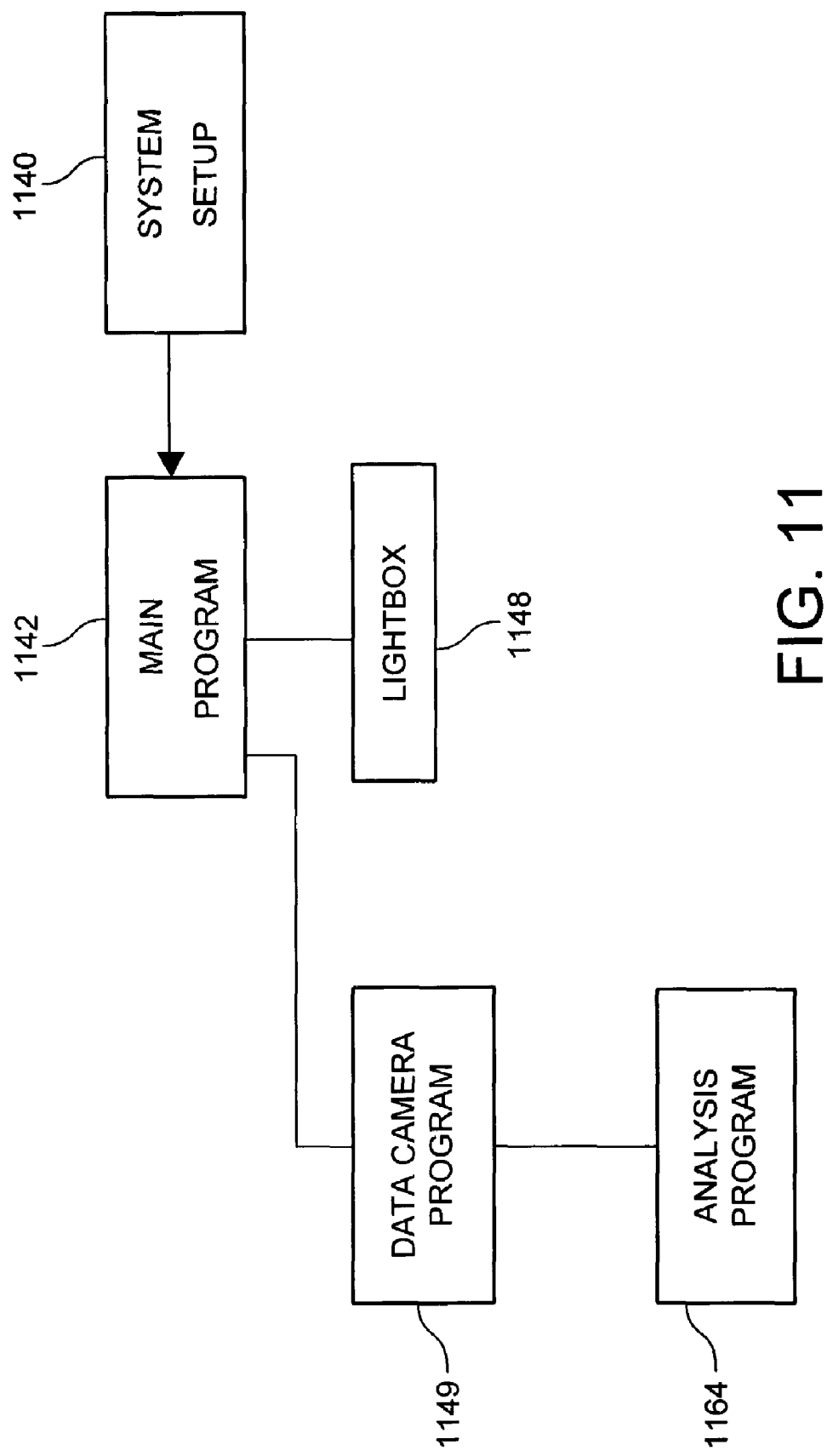
FIG. 11 illustrates a block diagram of a computer system according to one embodiment of the present invention.

Referring collectively to FIGS. 1, 3, and 11, which illustrate capture of a hyperspectral image of the desired region of the retina being examined, the retina is illuminated, for example, with white or filtered light from the exam light source 103 via the filter assembly 110, shutters (not shown) and a fiber optics cable 111, via internal fundus retinal imager optics (not shown), according to the system control program 1142. Such illumination is reflected off the various layers of the retina, through the fundus imager 302 and past the movable mirror 318 to the input to the hyperspectral imager 104 to a high resolution detector 306. After proper alignment, a data image is collected using a foot switch 360. Image data from the high resolution detector 306 is transferred to the data camera controller 358 via a data line 350 and a data interface 351. Image data is transferred to memory (which reformats the data, adds headers, and synchronizes the collection of the scene camera and high resolution detector data). Image data is also sent to a monitor 303, via the computer 358 and a data line 359 for screen display.

Figure 7:
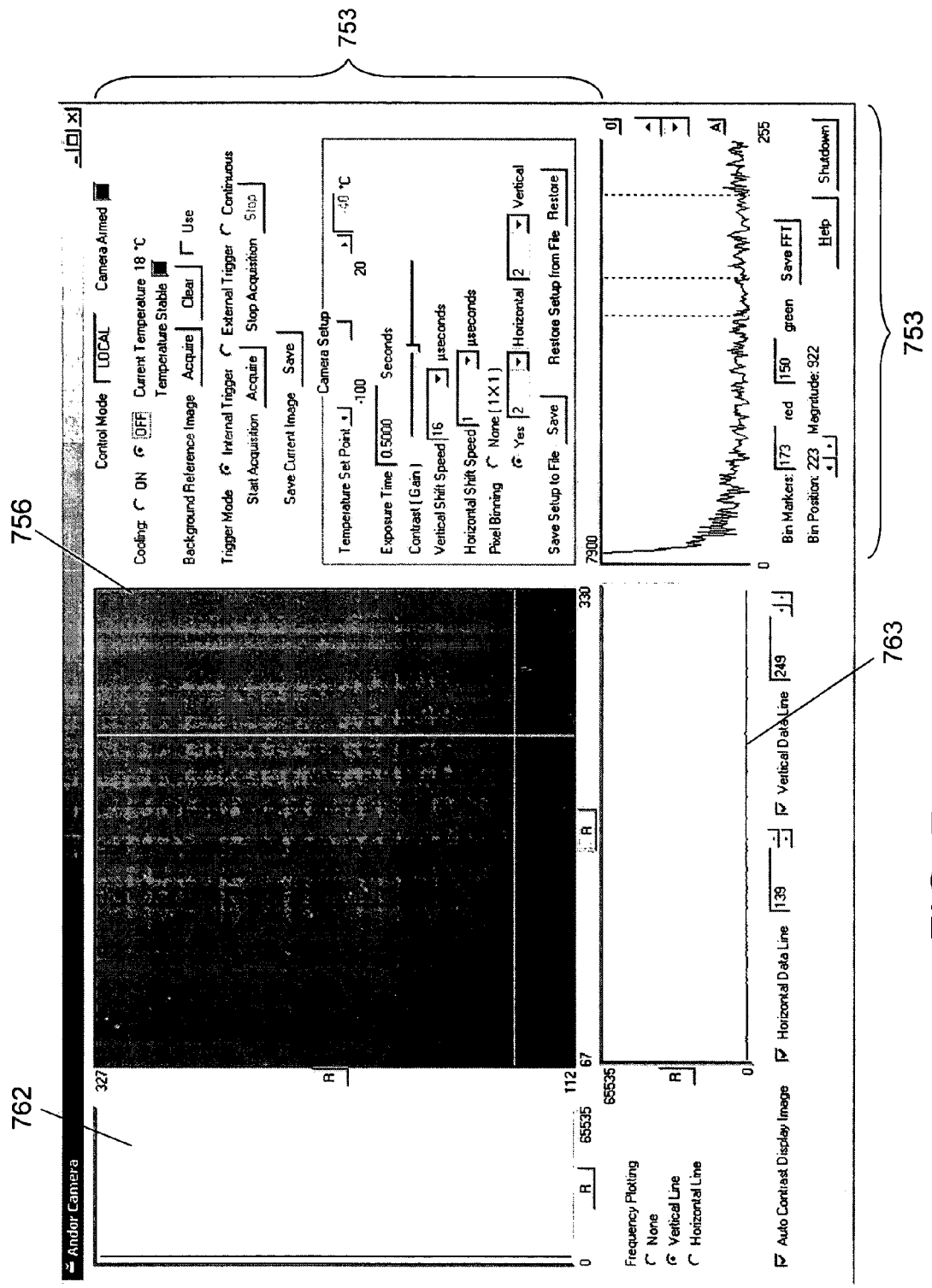
FIG. 7 illustrates a screen display of an example of a graphical user interface screen used to setup the imaging system according to one embodiment of the present invention, showing raw interferometric data and camera controls.

Referring to FIG. 7, a view of a sample screen display used to set up the system showing the raw interferometric data and camera controls is illustrated, according to one embodiment of the present invention. An acquisition window displays the most recent raw data image 756 from the data detector 106 (refer to FIG. 1) along with various intensity profiles 762 of the raw imagery, and Fourier transformed profiles 763. These can be displayed along with the scene camera live video image 559 (refer to FIG. 5B) from the scene camera detector 133 (refer to FIG. 1) and the location of the hyperspectral image 555 (refer to FIG. 5B). The main program software also is enabled to provide control of the various detector, timing, and illumination sources by way of input controls 753.

Raw interferometric data 756 is converted through calibration, and the information is presented for pathological analysis consists of several distinct steps.

In another embodiment of the present invention, the operators are enabled to vary the total energy transmitted to the eye by adjusting the operation of the various shutters (not shown) and the filters settings 348, 110 (refer to FIGS. 1 and 3). These illumination variations are controlled automatically or manually through operator selected settings.

Figure 5A:
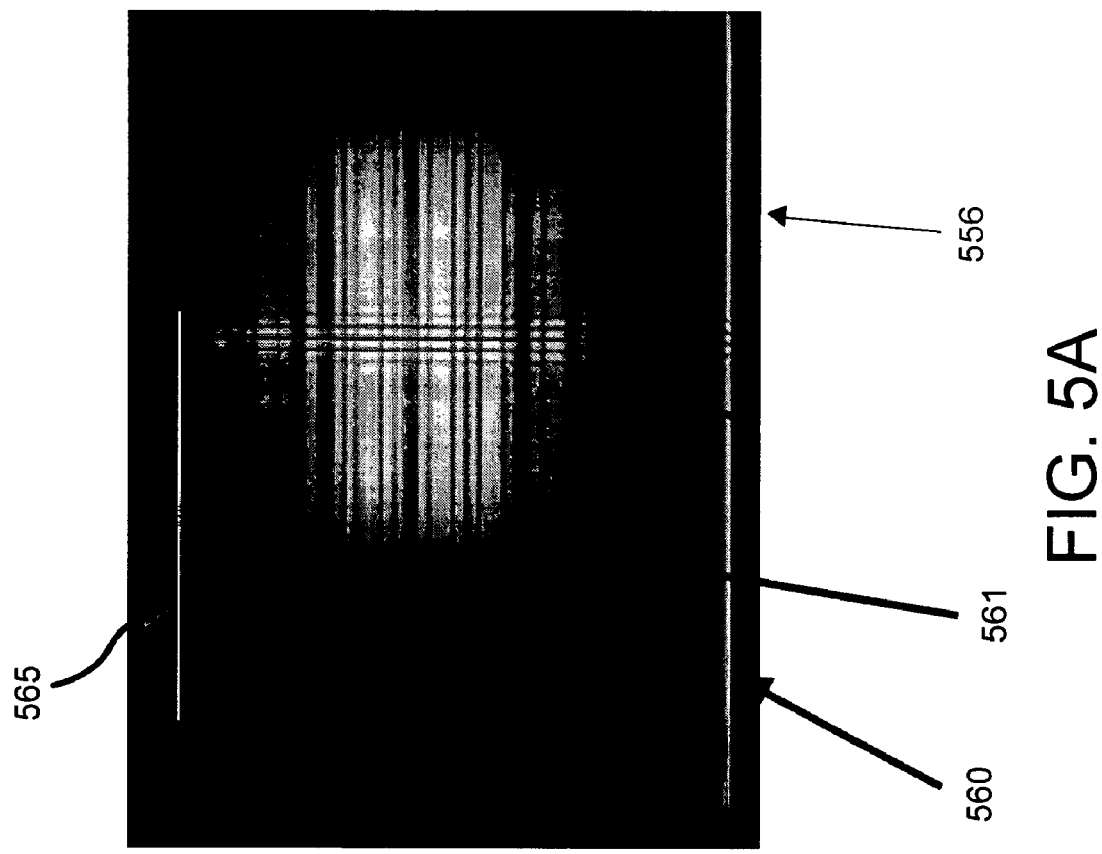
FIG. 5A illustrates an example of an image recorded by a hyperspectral imager detector with the calibration sources annotated according to one embodiment of the present invention.

Referring to FIG. 5A, an example of an image recorded by a hyperspectral imager detector with the calibration sources annotated is illustrated according to one embodiment of the present invention. Minor variations within an illumination source are compensated for by using the observed flash intensity from a fiber optic input 111 (refer to FIG. 1), which is positioned 560 on every raw data frame below the image data 561. The output of this lamp can vary due to usage, settings, and random phenomena in a flash to flash basis. Therefore, it is useful to have a way to compensate for such variations. One method of calculating an imbedded illumination source signal includes estimating the illumination intensity made using the mean value, "$flash_{mean}$." This technique is based on knowledge that the amplitude of the interferogram at the center portion of the interferogram is directly proportional to total illumination. Therefore, this value, $flash_{mean}$, can be used to normalize the whole 2D interferogram. The normalization value is calculated as the mean intensity of three successive interferograms 556 at bins around the center burst. Flash intensity normalization is just the scaling of each individual interferogram by this value, for example as ($flash_{mean}$)/(flash).

A normalization procedure in the analysis subroutine 1164 (refer to FIG. 11) is applied to each spectral band separately, resulting in empirical correction of spectral variations in image intensity due to transmissivity and quantum efficiency of the instrument, and spectral variation in intensity of the illumination light source.

Figure 9:
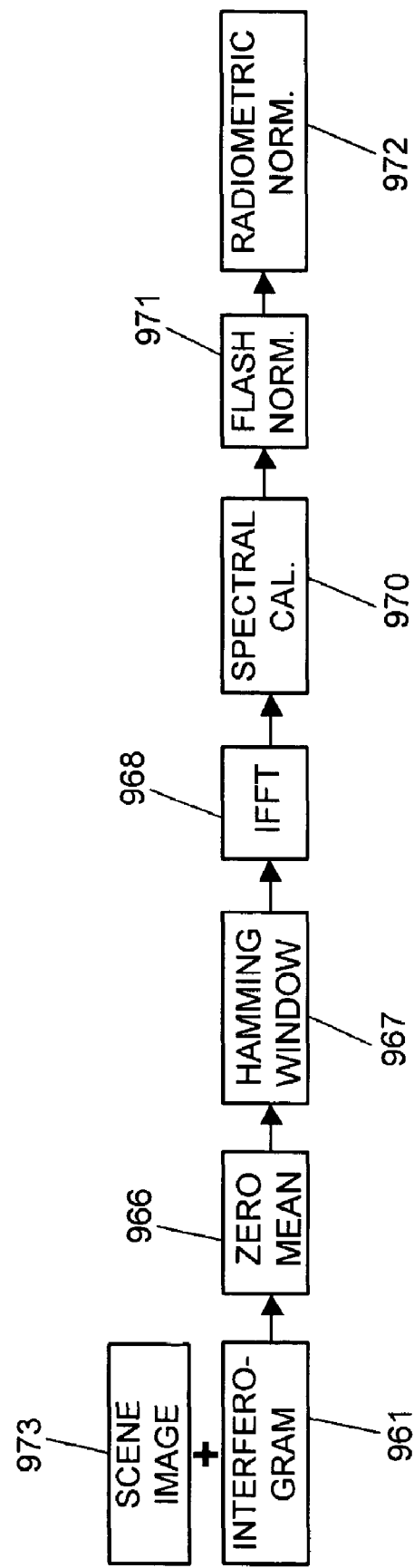
FIG. 9 illustrates a process for processing the hyperspectral interferometric data to recover a calibrated hyperspectral image according to one embodiment of the present invention.

Referring to FIG. 9, a flow diagram of algorithms employed for processing and calibrating the image in one embodiment of the present invention is illustrated. After collection of the raw image 961 with imbedded illumination source signal 560 and calibration signal 565 (refer to FIG. 5A), and scene image 973, each interference pattern from every spatial element is zero meaned 966. This step serves two purposes. Firstly, it produces data of zero mean. This is a good idea because the DC component does not contain spectral information. Secondly, it improves the signal-to-noise ratio of correlated components, which is useful in order to minimize the effects of noise. This "zero mean" step is realized by subtracting the running mean of the interferogram from the original interferogram. A single-pole, infinite impulse response (IIR) filter produces a running estimate of the mean of the interferogram $X_s(n)$. Mathematically, a zero mean filter is represented by the following difference equation $$X_{avg}(n)=\beta X_s(n-1)+(1-\beta)X_s(n),$$

where $X_{avg}$ is the running estimate of the mean, $X_s$ is the original interferogram, and $\beta$ is a smoothing parameter. The zero mean-ed interferogram is given by $$X_{zm}(n)=X_s(n-\beta)-X_{avg}(n).$$

These interference patterns are then processed with a Hamming filter 967 (refer to Bendat and Piersol, *Engineering Applications of Correlation and Spectral Analysis*, at pg 74), after which they are processed using an inverse Fourier transform 968 (refer to Bendat and Piersol, *Engineering Applications of Correlation and Spectral Analysis*, at pg 9). The purpose of the Hamming filter step is to taper the extremes of the interferogram so that any ringing effects introduced by the subsequent inverse Fast Fourier Transform step are minimized. The inverse Fast Fourier Transform (IFFT) step decodes the spectral information contained in the interferogram and produces uncalibrated data. The output of the IFFT is a symmetric spectrum having both the real and imaginary components. In this embodiment, only the real component of the spectrum is used.

A spectral calibration is then applied using the spectral calibration data 565 (refer to FIG. 5A) inserted above the image data 561 (refer to FIG. 5A) by fiber optics 175 (refer to FIG. 1). This is accomplished by noting in which bin number the major spectral peak from the spectral calibration source 369 (refer to FIG. 3) is located. This bin is then assigned the wavenumber corresponding to the known spectral wavenumber of the calibration source. Because a Fourier transform interferometer is linear in wavenumber and bin 0 is by definition 0 wavenumber all bins can be calibrated using a linear fit between zero and the bin that the calibration signal appears in 970. After spectral calibration the data are normalized for illumination intensity using the process described above 971. Radiometric normalization 972 is then performed.

In order to produce values in radiometric units (as opposed to digital numbers (DN)) it is useful to have a reference of known characteristics. The reference values according to embodiments of the present invention are given by the spectra of standard reflectance targets (SRT). Radiometric normalization data was collected by imaging 2, 5, and 10% SRT at a distance of 30 mm in front of the receiver optics of the fundus camera. Here the objective is to find the relationship between DN and reflectance. In this way, any new interferogram can be radiometrically normalized. First, the interferograms from the SRT are processed following the same steps described above. Then, all available data from the SRT is used to perform a linear regression in order to find the parameters that relate DN with reflectance. The linear regression algorithm finds the values of the parameters m, $a_0$ such that $$DN(n,\lambda)=m(n,\lambda)r(n,\lambda)+a_0(n,\lambda),$$

where DN is the resulting digital number, m is the slope of the line, r is the given reflectance, and $a_0$ is the intercept with the abscissa. The indices $(n,\lambda)$ make explicit the fact that these coefficients are calculated for each pixel in the FOV and each wavelength. The equation above is applied for every pixel in the FOV and for every wavelength of the spectra. This is for two reasons. Firstly, the linear regression is applied for every wavelength in order to take into account the wavelength-dependent response of the system according to its design. Secondly, it is applied for each pixel in the FOV in order to compensate for the low frequency spatial distortion introduced by imaging STR instead of actual eyes. This is due to the fact that the optics of the fundus camera has been designed to compensate for the optical qualities of the human eye.

In order to normalize actual data radiometrically, the inverse of the prior equation is applied, i.e., $$r(n, \lambda) = \frac{DN(n, \lambda) - a_0(n, \lambda)}{m(n, \lambda)},$$

so that, for any given DN, a value of normalized reflectance can be calculated.

Figure 10:
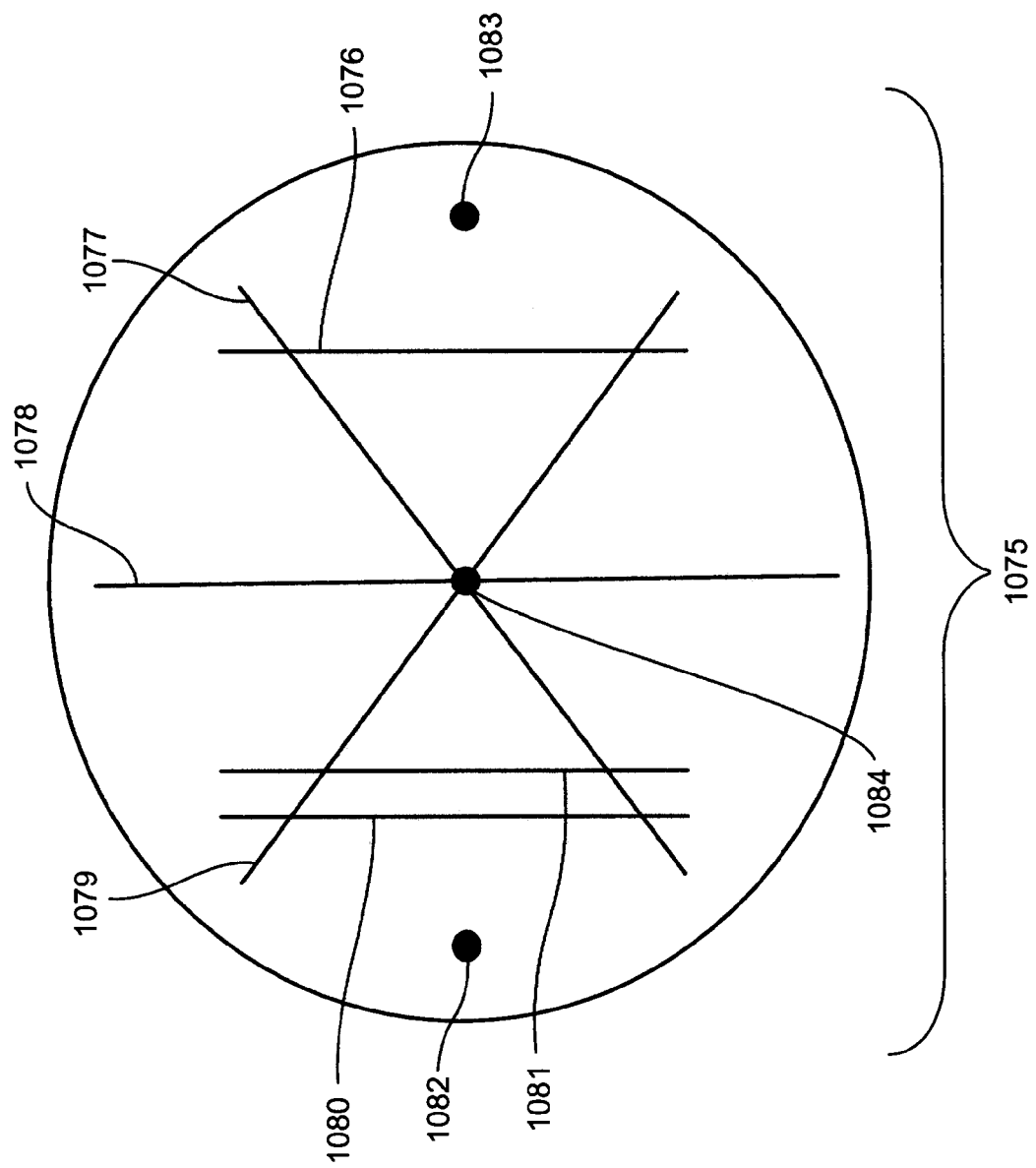
FIG. 10 illustrates a process for instrument alignment according to one embodiment of the present invention.

Referring to FIG. 10, a process for instrument alignment is illustrated for one embodiment of the present invention. Alignment of one embodiment of the present invention is verified during system startup by the main program 1142 (refer to FIG. 11). A calibration target 1075 is placed at the location of the object to be imaged such as the human retina and aligned with an imager such as a fundus camera 202 (refer to FIG. 2) having a particular field of view. This target has lines 1076, 1077, 1078, 1079, 1080, 1081 and dots 1083, 1084, 1082 placed as shown in FIG. 10 as brightly reflecting areas against a dark background.

Figure 8:
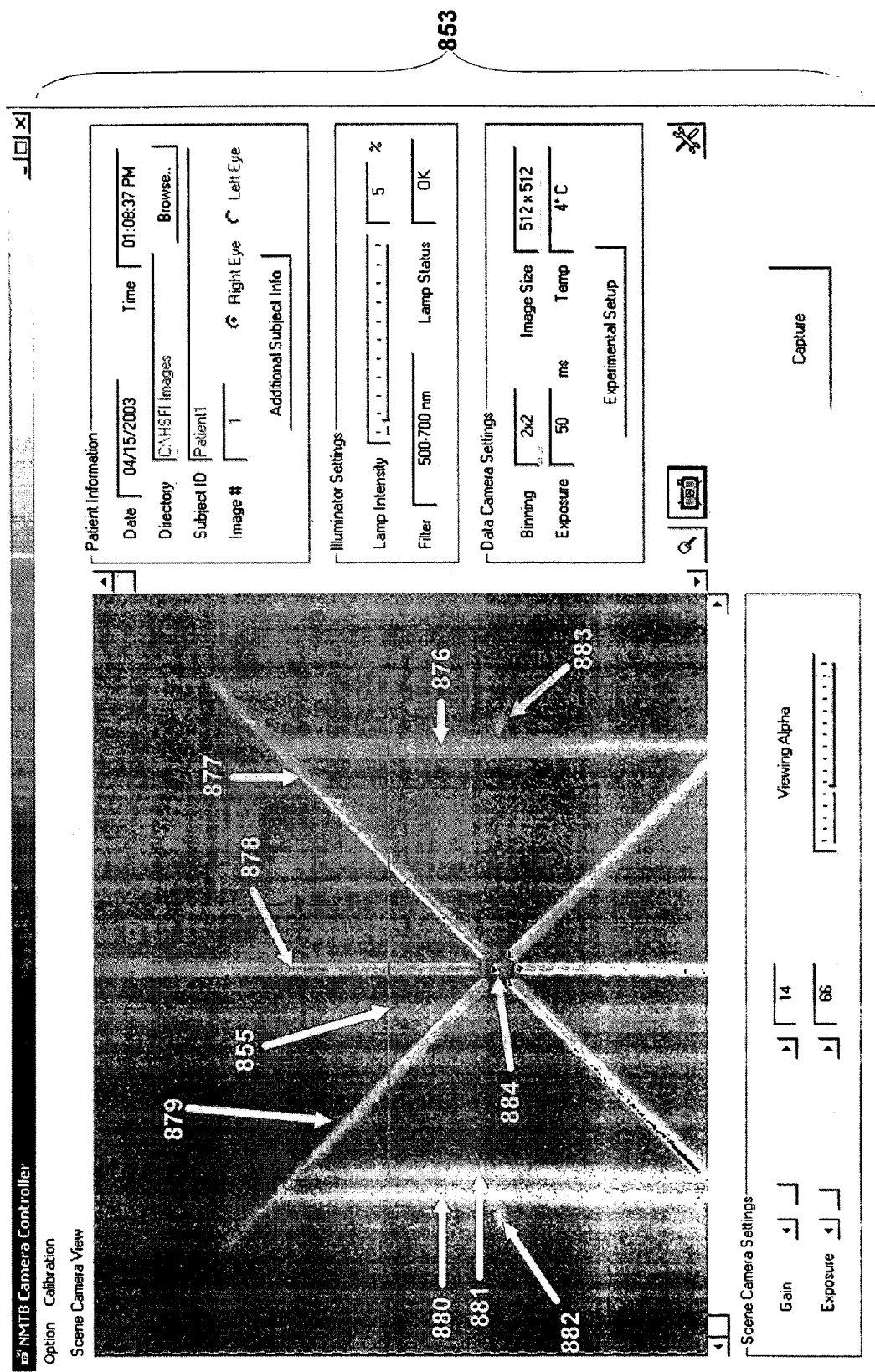
FIG. 8 illustrates a screen display of an example of a graphical user interface screen from a monitor incorporated in one embodiment of the present invention, showing the type of imagery used to align the fundus retinal imager and the data used to control and operate the system.

Referring to FIG. 8, a sample screen display 853 from one of the monitors illustrating the type of data used to control and operate the systems is illustrated for one embodiment of the present invention. The target lines 876, 877, 878, 879, 880, 881 appear in the scene camera image along with the hyperspectral reference line 855. The target lines 876, 877, 878, 879, 880, 881 and dots 883, 884, 882 are placed as illustrated in FIG. 8 and are viewed as contrasting points in comparison to the background image.

Referring to FIG. 11, a schematic of the computer system is illustrated according to one embodiment of the present invention. The analysis computer program subroutine 1164 uses lines 876, 877, 878, 879, 880 and dots 883, 884, 882 to determine if the reference hyperspectral line 855 (refer to FIG. 8) is located correctly with respect to the center of the image field of view defined by FOV dots 1082, 1083, 1084. This location is determined by which lines and dots are traversed by the hyperspectral line 855 and the position of those intersections on the scene image (refer to FIG. 8). The analysis computer program subroutine 1164 contains a database of values of number and position of intersections that determine the calibration status of the invention as aligned, marginally aligned, and misaligned. The analysis computer program subroutine 1164 also has the capability of emitting a message indicating the calibration status and the appropriate action to take, e.g. continue usage, repeat checking routine, or stop usage.

The analysis computer program subroutine 1164 also checks for the correct alignment of the Fourier Transform optics of the invention. This process uses the spectral calibration target 234 that consists of an integrating sphere which is placed in front of the fundus camera for the calibration process (refer to FIG. 2). The computer system takes a hyperspectral image of the spectral calibration target and locates the spectral signature that corresponds to the spectral calibration target. The analysis computer program subroutine 1164 compares this location to a predefined, stored set of values that determine the status of the alignment of the Fourier optics.

Once the hyperspectral image data has been obtained, the data is analyzed using principal component analysis (PCA), independent component analysis (ICA), and blind source separation (BSS) techniques to estimate sources of variability from information in recorded images, even if those sources are not completely statistically independent.

Optical changes that the detector captures result from retinal changes from one hyperspectral image to the next. The changes are mapped between recorded hyperspectral image frames. The ability to detect these changes is enabled by the increase in signal-to-noise ratio provided via embodiments of the present invention that incorporate the high efficiency spatially modulated Fourier imaging interferometer. The improved signal-to-noise ratio means that the resulting hyperspectral image signal contains detectable indications of retinal activity that rise above noise from various sources (for example, the lens transmission changes, changes in fluids in the eye through which energy passes, retinal background phenomena and other unknown physiological changes). In the case where retinal functioning is being measured, changes result from viewing the retina in a non-excited state versus and excited state are also recorded and areas of response mapped from areas that are non-responsive.

According to one embodiment of the present invention, principal components analysis (PCA) is used to isolate the signal representing the state of hemoglobin saturation over a passage of time. In another embodiment of the present invention, blind source separation (BSS) (using an extended spatial decorrelation (ESD) algorithm) and independent component analysis (ICA) (using the Fast-ICA algorithm) are used to extract a functional signal from retinal hyperspectral images. By comparison of images separated from one another in time, and applying the data analysis techniques of the present invention, measurements of changes in blood perfusion, metabolic activity, and hence the health status of the retina can be assessed. Depending upon the diagnostic parameter being sought, the time span between compared hyperspectral images may be as short as a few milliseconds or as long as weeks or months.

Independent component analysis (ICA) is a statistical and computational technique used to reveal hidden factors that underlie a set of random variables, in this case, measurements of reflectance from a retina. The goal is to recover independent sources given only the sensor observations that are unknown linear mixtures of the unobserved independent source signals. Thus ICA is use to analyze mulitvariate data stemming from the production of images of the retina. ICA is related to Principle Component Analysis (PCA) and factor analysis but is more capable of finding underlying sources or factors in a data set because it takes into account higher order statistical properties of the data. For example, PCA is a correlation based transformation of data. In contrast, ICA not only decorrelates the signals (i.e. $2^{nd}$ order statistics) but also reduces the higher order statistical dependencies (i.e. $4^{th}$ order cumulants) and attempts to make the signals detected as statistically independent as possible. In ICA, data sources are assumed to be linear mixtures of unknown variables.

Blind Source Separation (BSS) is a similar technique as ICA, but in this case only second order statistics are used. BSS and ICA are applied in the present invention to separate sources of variability present in hyperspectral images of the retina produced by the apparatus of the present invention.

In an embodiment of the present invention, a metabolic function of the retina is isolated using principal component analysis (PCA). PCA determines an appropriate subspace of dimensionality smaller than the dimensionality of the original feature space of the hyperspectral images. Using PCA, the functional signal can be reconstructed using a subset of the principal components. The data set has the time series of each pixel in the image, and the principal components can be found as the solution of $$SV = \Lambda V'$$

where S is the sample covariance matrix of the data set and its elements are given by $$S_i = \frac{1}{N_i - 1} \sum (x_{ij} - \bar{x}_i)(x_{ij} - \bar{x}_i)^T$$

where the $x_{ij}$ are the pixel values of the observed sources.

The matrix V contains the eigenvectors $v_n$ and $\Lambda$ is the diagonal matrix of the eigenvalues $\lambda_n$, which represents the variance of the data along the principal axes. The matrix V is orthogonal and the eigenvectors are normalized and orthogonal to each other, that is $$v_i^T v_i = 1$$

$$v_i^T v_j = 0 \; \forall i \neq j$$

The n-th principal component is given by $$y_n = \lambda_n^{-1/2} v_n^T X$$

The functional signal X can be reconstructed using a combination of the principal components, and can be calculated by $$\hat{X} = \sum_n v_n(v_n^T X) = \sum_n v_n \lambda_n^{1/2} y_n$$

In practice of the above-described signal analysis technique it has been generally found that the principal components 2 through 5 potentially contain meaningful information on the functional signal, while the remaining principal components do not appear to have any useful information.

In another embodiment of the present invention, data preparation procedures produce image data with approximately 111 spectral bands of 87 wavenumber resolution between 450 nm and 800 nm over 512 spatial elements approximately 25 microns in size, with values strongly correlated to percent reflectance of calibration targets and, by inference, features on subjects' fundus. The inverse Fourier transform produces uncalibrated data, i.e., the bins of the output are not yet related to a set of wavelengths. Spectral calibration, the process by which each bin is assigned a wavelength, is realized by noting the output of the inverse Fourier transform to a known source. According to an embodiment of the present invention, the calibration source is a mercury lamp whose light is fed into the first pixels of the Hyperspectral Fourier Transform Spectrometer's field of view through a fiber optic probe. Specifically, each 2D interferogram contains the spectral signature of the lamp being used to illuminate the subject being imaged. The wavelength values of the bins are assigned, for example, by noting the bin at which the 435 nm peak of the mercury lamp's light spectrum appears and assigning the first bin to 0 nm.

Another embodiment of the present invention allows the imager to collect hyperspectral images of the retina of eyes with various sized pupils such as are found in animals used in research. To accommodate for different sized pupil the input and output apertures of fiber optics 111 (refer to FIG. 1) are increased or decreased depending on if the pupil is larger or smaller respectively. Changes are made to the fundus imager 202 (refer to FIG. 2) to increase or decrease its aperture size depending on if the pupil is larger or smaller respectively, the exact sizes which, as those familiar with the art will know, can be readily calculated using an analytic optical model of the fundus imager. No changes to the hyperspectral imager 104 (refer to FIG. 1), scene camera 133 (refer to FIG. 1), data camera 206 (refer to FIG. 2), light source 103 (refer to FIG. 1), calibration sources 111, 369, or computer control systems implementing the main control program 1142 (refer to FIG. 11) are then required.

Whereas the drawings and accompanying description have shown and described the preferred embodiment of the present invention, it should be apparent to those skilled in the art that various changes may be made in the form of the invention without affecting the scope thereof. Further, while certain specific uses of the invention have been illustrated, it will also be apparent to those skilled in the art that a wide variety of retinal pathologies may be imaged and analyzed using the optical collection techniques and equipment described herein together with the advanced statistical analysis techniques disclosed. For example, such pathologies as Age-related Macular Degeneration (AMD), Glaucoma, Diabetic Retinopathy, Cystoid Macular Edema, and other diverse macular diseases will all benefit from application of the techniques and technology described herein. Additionally, to the extent that metabolites have a spectral component that is subtly different other retinal spectral signatures, this invention is useful to differentially detect such metabolites.

What is claimed is:

1. An apparatus for measuring a spectral intensity of a retina as a function of wavelength for a spatial region of the retina, the apparatus comprising:
   an optical device for viewing the spatial region of the retina, the optical device being optically connected to a high efficiency spatially modulated Fourier imaging Interferometer;
   an illumination source for illuminating the spatial region; and
   at least one detector for detecting a spectral signature of a spatial region imaged.

2. The apparatus for measuring a spectral intensity of a retina as a function of wavelength for a spatial region of the retina as described in claim 1, wherein the spatial region of the retina is illuminated by a single exposure of light.

3. The apparatus for measuring a spectral intensity of a retina as a function of wavelength for the spatial region of the retina as described in claim 1, further comprising a calibration source.

4. The apparatus of claim 1 wherein the optical device is a fundus imager.

5. An apparatus for measuring a spectral intensity of a scene as a function of wavelength for a spatial region of the scene, the apparatus comprising:
   a high efficiency spatially modulated Fourier imaging interferometer;
   a fundus manager for observing a spatial region to be illuminated;
   means for illuminating the spatial region with a single exposure of light;
   means for collecting light from the spatial region illuminated;
   optics adapted to pass collected light from the spatial region illuminated through the interferometer to one or more detectors thereby creating an image;
   means far measuring an intensity from an illumination source with a calibration source; and
   an output monitor for displaying a calibrated spectral signature of the spatial region.

6. A method for measuring a spectral intensity of a retina as a function of wavelength for a spatial region of the retina, the method comprising:
   observing the spatial region with an optical device;
   illuminating the spatial region with a single exposure of light;
   collecting the light from the spatial region illuminated;
   passing collected light through a high efficiency spatially modulated Fourier interferometer to one or more detectors;
   calibrating an image collected with a signal measured from a calibration source; and
   viewing a calibrated spectral signature of the spatial region.

7. A method for assessing metabolic function change of a retina based on hyperspectral images of the retina, the method comprising:
   illuminating a spatial region of a retina with a single exposure of light at a first time;
   collecting the light from the spatial region illuminated at the first time;
   passing light collected at the fast time through a high efficiency spatially modulated Fourier interferometer to one or more detectors;
   calibrating a first hyperspectral image of the retina from the light passed through the high efficiency spatially modulated Fourier interferometer at the first time with a signal measured from a calibration source at the first time;
   recording the first hyperspectral image;
   illuminating the spatial region of the retina with a single exposure of light at a second time;
   collecting, the light from the spatial region illuminated at the second time;
   passing light collected at the second time through the high efficiency spatially modulated Fourier interferometer to the one or more detectors;
   calibrating a second hyperspectral image of the retina from the light passed through the high efficiency spatially modulated Fourier interferometer at the second time with a signal measured by the calibration source at the second time;
   recording the second hyperspectral image; and
   assessing metabolic function change of the retina based upon differences in spectral intensity between the first image and the second image.

8. The method for assessing metabolic function change of a retina as recited in claim 7, wherein assessing comprises applying principal components analysis to the reflectance differences.

9. The method for assessing metabolic function change of a retina as recited in claim 7, wherein assessing comprises applying a fast-Independent Component Analysis algorithm to the first and second images.

10. The method for assessing metabolic function change of a retina as recited in claim 7, wherein assessing comprises applying an extended spatial decorrelation algorithm to the images.

* * * * *